United States Patent
Mount

[11] Patent Number: 5,345,774
[45] Date of Patent: Sep. 13, 1994

[54] METHOD AND APPARATUS FOR ZERO EMISSIONS TESTING OF A REFRIGERANT IN A CLOSED SYSTEM

[75] Inventor: Gordon L. Mount, West Monroe, N.Y.

[73] Assignee: Carrier Corporation, Syracuse, N.Y.

[21] Appl. No.: 11,874

[22] Filed: Feb. 1, 1993

[51] Int. Cl.[5] .................................. F25B 49/00
[52] U.S. Cl. .......................... 62/127; 73/23.42; 422/103; 436/39
[58] Field of Search ................. 436/39; 422/103; 73/23.42, 61.56; 62/127, 125

[56] References Cited

U.S. PATENT DOCUMENTS

| | | | |
|---|---|---|---|
| 4,110,998 | 9/1978 | Owen | 62/125 |
| 4,923,806 | 5/1990 | Klodowski | 436/39 |
| 5,071,768 | 12/1991 | Klodowski | 62/127 X |
| 5,214,931 | 12/1992 | Paige | 62/125 |

Primary Examiner—William E. Wayner

[57] ABSTRACT

An external fluid circuit capable of being connected between service valves provided on a closed system containing a refrigerant. The external fluid circuit is provided with a testing tube and testing tube holder. A flow meter and flow regulator are connected in series in the external fluid circuit. The flow meter is provided with a transparent chamber containing a float indicator member to indicate when a desired rate of refrigerant flow through the circuit has been achieved. A three-way toggle valve is provided between the flow meter and testing tube holder allowing the refrigerant to be directed through the testing tube or through a bypass loop. A hand-held compressor downstream of the testing tube holder induces sufficient flow pressure difference where there is insufficient system pressure to cause proper flow through the external fluid circuit.

26 Claims, 3 Drawing Sheets

METHOD AND APPARATUS FOR ZERO EMISSIONS TESTING OF A REFRIGERANT IN A CLOSED SYSTEM

BACKGROUND OF THE INVENTION

1. Field of the Invention

This invention relates in general to the testing of refrigeration systems and, in particular, to an apparatus and method for detecting contaminants in a refrigerant flowing through a closed system without discharging the refrigerant into the atmosphere.

2. Discussion of the Prior Art

The art of refrigerant testing has been advanced by the device disclosed in U.S. Pat. No. 4,932,806 issued to Klodowski and assigned to the assignee of the present application. The disclosure of this patent is herein incorporated by reference.

The invention disclosed in the Klodowski patent is directed to a process and device for quantitavely testing for contaminants in a refrigerant flowing in a closed system. A single test is utilized without drawing more refrigerant than is needed for the test. The Klodowski test is valid whether the contaminants are liquid or vapor, whether the system is operating or not, and is adaptable for high or low pressure usage. The Klodowski device employs a fluid hose having a hose line and two fluid tight connectors on either end of the hose line. One of the connectors is connected to a testing tube holder having a testing tube contained in a testing tube container. The testing tube holder has a flow restrictor positioned on the upstream side to regulate the incoming refrigerant to a desired rate of flow. To conduct the test, the other connector is secured to a service valve provided on the discharge line of the closed system containing the refrigerant. The service valve is then opened. Refrigerant under pressure within the closed system is thereby allowed to discharge through the discharge line and the service valve into the hose line. The refrigerant then passes through the flow regulator and attains the desired rate of flow. It next passes into the testing tube wherein the test for containments is conducted. After the refrigerant passes through the testing tube, the tested refrigerant is continuously discharged from the tube container into the atmosphere. Thus, the Klodowski device is limited to the testing of refrigerants contained within systems having a pressure greater than atmospheric pressure. Discharge of certain refrigerants is considered an environmental hazard.

OBJECTS AND SUMMARY OF THE INVENTION

It is, therefore, an object of the present invention to improve devices and processes for the testing for contaminants within a refrigerant.

It is a further object of the present invention to adapt a refrigerant testing device to a closed system containing a refrigerant wherein the internal pressure of the closed system can be lower than atmospheric pressure.

Still another object of the present invention is to test refrigerants in a closed system for contaminants without discharging the tested refrigerant into the atmosphere.

An additional object of the present invention is to enable a refrigerant testing device to be connected to service valves in fluid communication with a closed system containing a refrigerant wherein the pressure difference between the valves is great enough to provide an adequate rate of flow through the testing device.

Still another object of the present invention is to enable a refrigerant testing device to conduct a test for contaminants in the refrigerant of a closed system when the pressure difference between service valves of the closed system is insufficient to cause the refrigerant to flow through the device.

These and other objects are attained in accordance with the present invention wherein an external fluid circuit is capable of being connected between service or isolation valves provided on a closed system containing a refrigerant. The external fluid circuit is provided with a testing tube and testing tube holder having an upstream open end and a downstream open end relative to the direction of refrigerant flowing through the external fluid circuit. A flow meter is connected in series in the external fluid circuit and is positioned on the upstream side of the testing tube. The flow meter is provided with a transparent chamber containing a float indicator member to indicate when the desired rate of refrigerant flow through the circuit has been achieved. The flow regulator is connected in series with the circuit and is positioned on the upstream side of the flow meter. The flow regulator allows the flow of refrigerant to be adjusted to a desired rate of flow. A three-way toggle valve is provided between the flow meter and testing tube holder allowing the refrigerant to be directed through the testing tube or through a bypass loop.

To conduct the test for contaminants in the refrigerant, the external fluid circuit is connected to first and second isolation valves provided on the closed system. The three-way toggle valve is set so that the fluid flowing through the circuit is directed through the bypass loop of the circuit and not through the testing tube. The flow regulator is then slowly opened to adjust the flow to the desired rate as shown by indicia provided on the flow meter. Once the flow rate has been adjusted to the desired rate of flow, the three-way toggle valve is flipped to direct the flow of refrigerant through the testing tube. The downstream sides of both the testing tube and the bypass loop are connected to the second isolation valve to return the fluid passing through the circuit back into the closed system. Once the test is completed, the isolation valves can be closed and the external fluid circuit removed from the closed system. In the event the pressure difference between the isolation valves provided on the closed system is insufficient to cause the desired rate of flow through the external fluid circuit, a small compressor is provided on the downstream side of the testing tube holder. The downstream sides of the testing tube holder and of the bypass loop are both connected in fluid communication with the suction line of the compressor. The discharge line of the compressor is connected directly to the second isolation valve. The compressor thus achieves a sufficient flow rate through the external fluid circuit.

The testing tube is serially provided with, from the upstream end to the downstream end, a demisting section followed by a contaminate-indicating section. The contaminate indicating section is provided with a first length of rolled brass screen, a glass fiber disk, a water removal and moisture indicating section, a second glass fiber disk, a second length of rolled brass screen, a third glass fiber disk and an acid indicating section. Both the acid indicating section and the moisture indicating section are provided with indicia for determining the amount of contaminate.

BRIEF DESCRIPTION OF THE DRAWING

Further objects of the present invention together with additional features contributing thereto and advantages accruing therefrom will be apparent from the following description of a preferred embodiment of the present invention which is shown in the accompanying drawing, wherein.

DETAILED DESCRIPTION OF A PREFERRED EMBODIMENT

Figure 1:
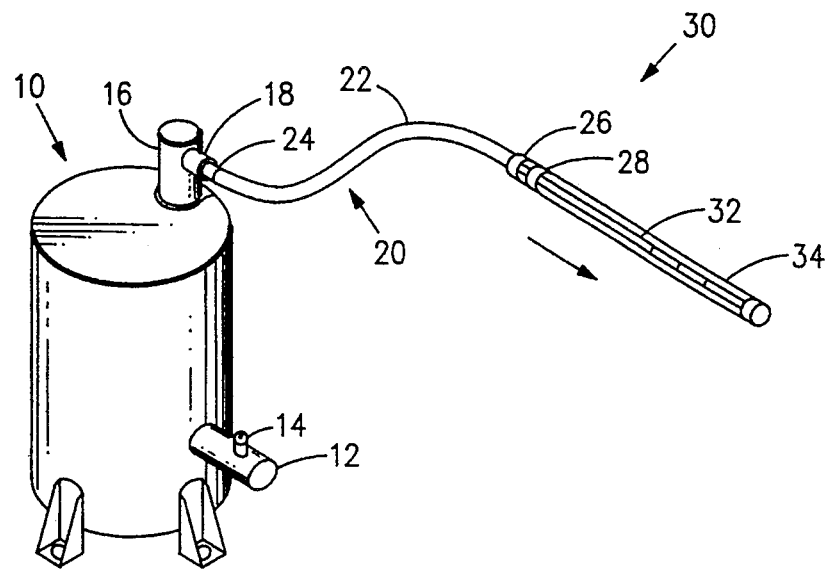
FIG. 1 is a perspective view of a prior art test device connected to the compressor of a closed refrigeration system.
Figure 2:
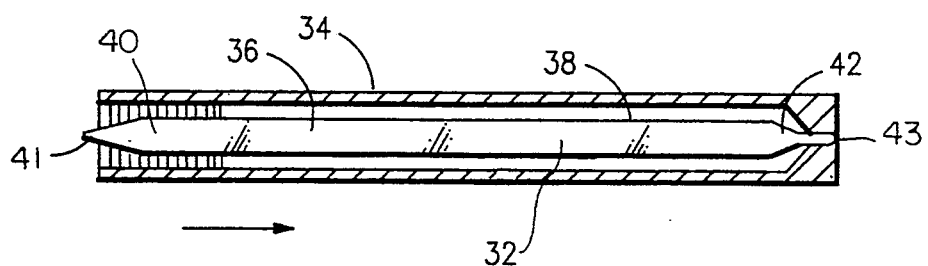
FIG. 2 is a partially exploded view of the prior art refrigerant testing tube container shown in FIG. 1.
Figure 3:
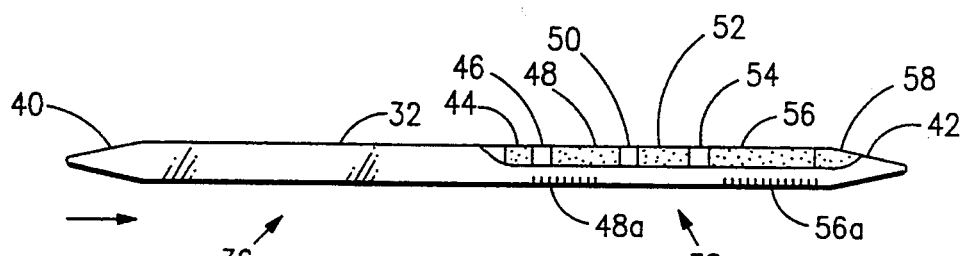
FIG. 3 is a partially cut away side evaluational view of the prior art contaminant testing tube of FIG. 2.

Referring now to FIG. 1 wherein there is shown a compressor 10 in conjunction with a prior art testing tube holder 30. The compressor 10 is representative of any compressor utilized in an air conditioner, chiller, heat exchanger or similar closed system having a compressor for compressing a refrigerant. The compressor 10 would typically have a suction line 12 with a service valve 14 connected thereto for providing input access into the closed system. A discharge line 16 would also typically be provided on the compressor 10, with a similar service valve 18 to allow the closed system to be flushed of internal fluids. The prior art refrigerant testing device includes the testing tube holder 30 composed of a testing tube 32, a testing tube container 34 and a flow restrictor 28. The prior art testing tube holder 30 is connected to service valve 18 of the discharge line 16 of compressor 10 by a fluid hose 20. Fluid hose 20 includes a connector 24, typically employing a Schraeder type fitting, which is connected to the service valve 18. Another connector 26 on the hose 20 is connected to the flow restrictor 28. FIG. 2 shows the prior art testing tube 32 secured within the testing tube container 34. Shown in FIGS. 2 and 3 is a demisting section 36 and a contaminant-indicating section 38 of testing tube 32. The testing tube 32 has an upstream end 40 whose tip has an upstream opening 41 relative to the direction of flow of refrigerant through the testing tube 32 indicated by the arrow in FIG. 2. A downstream end 42 on the prior art testing tube 32 also has at its tip a downstream opening, i.e., downstream relative to the direction of refrigerant flow. The tips of the ends 40 and 42 are breakable and are broken off to create the end openings, 41 and 43, respectively, just prior to conducting the test for contaminants. The testing tube 32 is utilized to detect the amount of water and acid that may be present in the refrigerant contained in the closed system. This is achieved in the testing tube by demisting section 36 for oil removal followed by the contaminant-indicating section 38.

To conduct a test for contamination, the flow restrictor 28 of testing tube holder 30 is connected to connector 26 of fluid hose 20 which in turn is connected to service valve 18 of discharge line 16 by the connector 24 of fluid hose 20. The service valve 18 is opened to allow refrigerant from the closed system to flow through the hose line 22 and through the flow restrictor 28. The flow restrictor 28 regulates the flow of refrigerant therethrough to a desired rate of flow for testing purposes. The refrigerant then flows through the testing tube 32 from the upstream end opening 41 and is discharged into the atmosphere from the downstream end opening 43 after the refrigerant is tested in the contaminant-indicating section 38.

As shown in FIG. 3, the contaminant-indicating section 38 includes, in series from the upstream end 40 toward the downstream end 42, a first length of rolled brass screen 44, followed by a first glass fiber disc 46 which in turn is followed by a water removal and moisture indicating section 48. The moisture indicating section 48 is provided with moisture sensitive indicia 48a to indicate the amount of moisture present in the refrigerant. The moisture indicating section 48 is followed by a second glass fiber disc 50, a second length of rolled brass screen 52 and third glass fiber disc 54, which in turn is followed by an acid indicating section 56. The acid indicating section 56 is provided with acid sensitive indicia 56a to indicate the amount of acid present in the refrigerant. The acid indicating section 56 is followed by a third length of rolled brass screen 58.

The moisture indicating section 48 includes silica sand chemically treated with two coats of cobaltous chloride by a process well known in the art. The cobaltous chloride turns from blue to pink when exposed to moisture. The acid indicating section 56 includes bromophenol blue on a glycerol fiber coating a silica sand base which will change from blue to yellow in the presence of mineral acids. The process for making the chemically treated silica sand for the acid indicating section 56 is also well known in the art.

A variety of methods for determining the amount of moisture content in the refrigerant have been disclosed in the prior art. These methods include identifying the length of color change indicted by the moisture indicating indicia 48a and comparing it to empirically determined, time dependant base data; matching color-coded indicating cards with the final color attained in the moisture indicating section 48; or timing the duration of a color change in the section 48 and matching the attained color with a time dependant color-coded indicating card. The acid content of the refrigerant can be determined by a prior art method which includes timing the color change in the acid indicating section, identifying the number on the acid indicating indicia 56a which indicates where the color change stopped and entering this collected data into an empirically determined acid indicator table.

Figure 4:
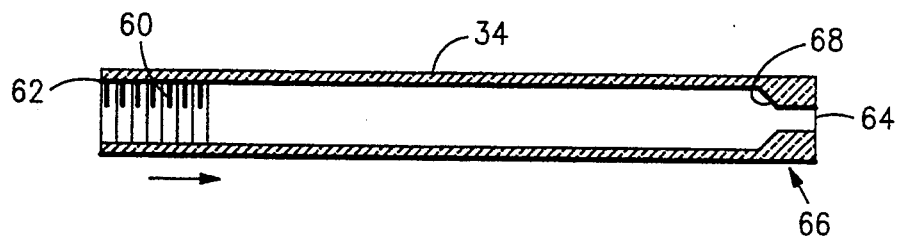
FIG. 4 is a longitudinal sectional view of the prior art testing tube container.

Referring now to FIG. 4 wherein there is shown the prior art testing tube container 34 having an upstream end and 62 and a downstream end 64. The upstream end 62 is provided with an internally threaded surface 60 which can receive, in a fluid-tight fit, the flow restrictor 28. The downstream end 64 is provided with a support member 66 having an annular beveled surface 68. As shown in FIG. 2, the beveled surface 68 aids in securely supporting the testing tube 32 within the testing tube container 34.

Figure 5:
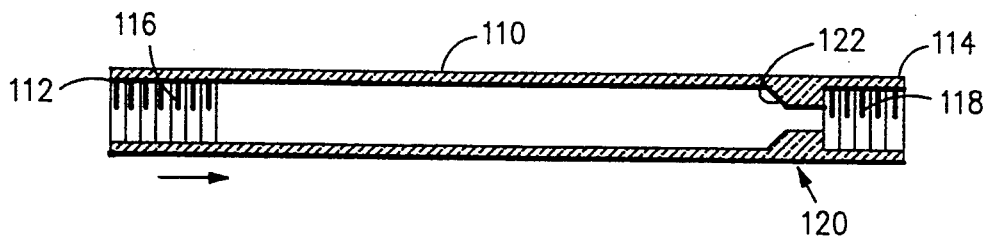
FIG. 5 is a longitudinal sectional view of the testing tube container of the present invention.

FIG. 5 shows the preferred embodiment of a testing tube container 110 in accordance with the present invention. The testing tube container 110 has an upstream end 112 and a downstream end 114. Each of the ends 112 and 114 has an internally threaded end portion 116 and 118, respectively, and the downstream end 114 is provided with a tube support member 120 having an annular beveled surface 122 for supporting a testing tube.

Figure 6:
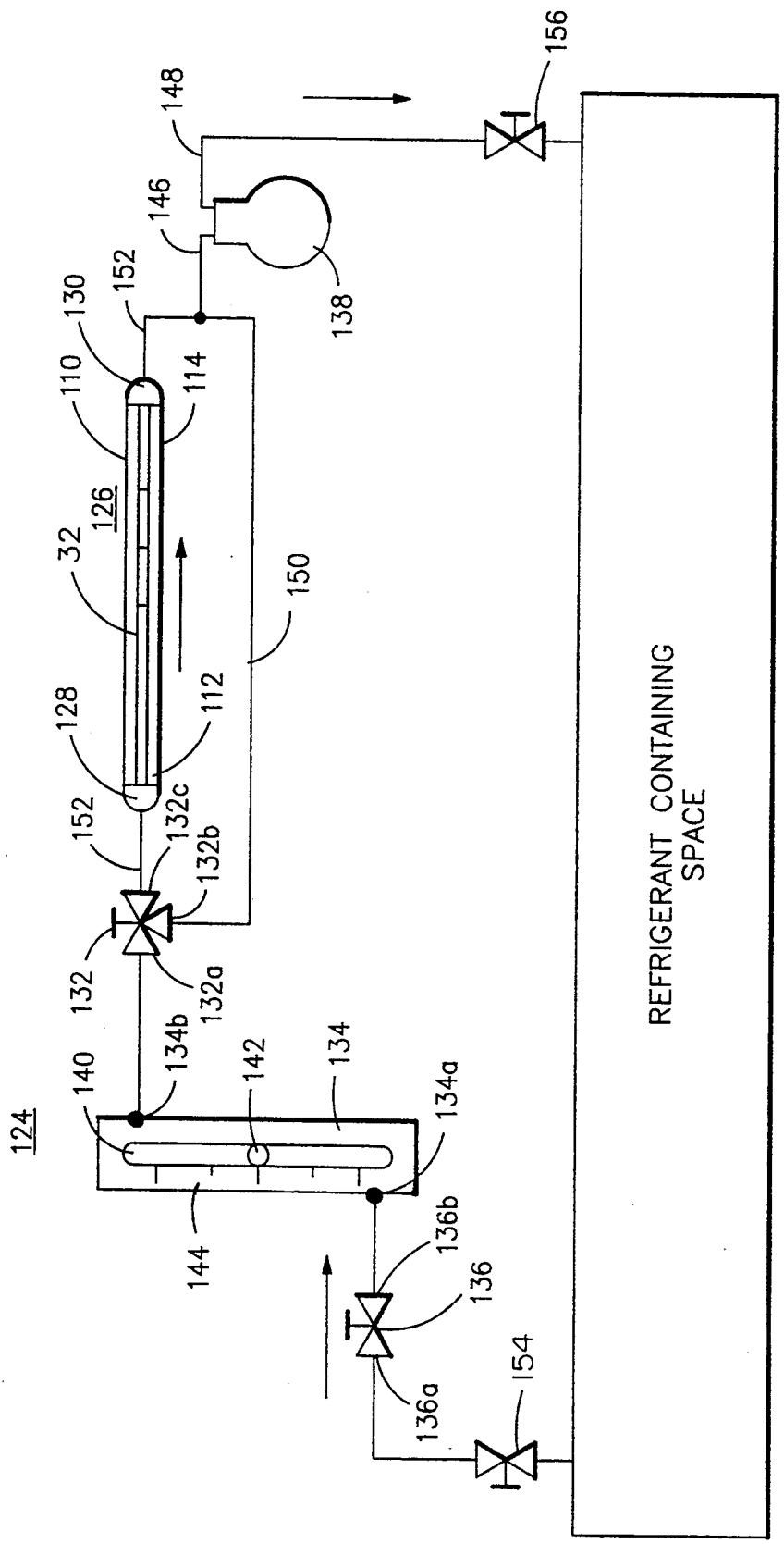
FIG. 6 is a schematic view of the external fluid circuit of the present invention.

FIG. 6 illustrates an external fluid circuit apparatus 124 in accordance with the present invention. The fluid circuit apparatus 124 includes a testing-tube holder assembly 126 composed of a testing tube 32 contained within the testing tube container 110. The container 110 has an upstream connector 128 and a downstream connector 130 as shown in schematic in FIG. 6. The connectors 128 and 130 are secured in a fluid tight fit to the internally threaded end portions 116 and 118, respectively, of the testing tube container 110 as shown in FIG. 5. The external fluid circuit apparatus 124 also includes a three-way toggle valve 132, a flow meter 134, a flow regulator or needle valve 136 and a small hand-held compressor 138. The three-way toggle valve 132 is provided with an inlet port 132a, a first outlet port 132b and a second outlet port 132c, while the needle valve 136 is provided with an upstream port 136a and a downstream port 136b. The flow meter 134 has a transparent flow indicating chamber 140 that contains a free-floating flow-responsive member 142. Flow line indicia 144 inscribed along the side of the chamber 140 indicate the rate of flow of refrigerant through the external fluid circuit 124. The flow meter 134 is also provided with an upstream intake port 134a and a downstream discharge port 134b. The small compressor 138 has a suction line 146 for receiving fluid and discharge line 148 for discharging fluid.

The external fluid circuit apparatus 124 is also provided with a bypass loop 150 and a detecting loop 152 as shown in schematic in FIG. 6. The bypass loop 150 connects the first outlet port 132b of the three-way toggle valve 132 directly to the suction line 146 of the small compressor 138. The testing tube holder 126 of the present invention is connected in series in the detecting loop 152 and is positioned between the second outlet port 132c of the three-way toggle valve 132 and the suction line 146 of the small compressor 138. The preferred location of the small compressor 138 is on the downstream side of the testing tube holder 126. In this location within the circuit 124, the compressor 138 will not cause condensation of vaporized refrigerant prior to the refrigerant entering the testing tube 32.

The component parts of the external fluid circuit apparatus 124 are connected in fluid communication with one another in the relative positions shown in FIG. 6 by Schraeder type fittings and refrigerant hose lines of types well known in the art. The assembled circuit apparatus 124 is light-weight, portable and easily carried by a refrigeration service person. The testing tube 32 is used to conduct a single test and is readily replaced by a fresh, unused testing tube for a subsequent test.

FIG. 6 also shows a refrigerant containing space that represents any portion of the closed system containing the refrigerant. The closed system would typically contain a first isolation valve 154 and a second isolation valve 156. The isolation valves 154 and 156 may be the service valves provided on the suction and discharge lines of the compressor of the closed system or, alternatively, could be first and second service valves placed anywhere in the closed system being accessible to a service person. The pressure difference between the isolation valves 154 and 156 may be sufficiently great to cause the desired rate of flow of refrigerant through the inventive external fluid circuit 124, thus removing the need for the small compressor 138 in order to conduct the contaminant test.

The preferred embodiment of the present invention including the small compressor 138 renders the inventive external fluid circuit 124 particularly well suited to conduct tests on closed systems in which there would be little if any pressure difference between the isolation valves 154 and 156.

The apparatus of the present invention, unlike prior art refrigerant testing devices which are open to the atmosphere, can be utilized on closed systems wherein the internal pressure of the system is less than atmospheric pressure or wherein the system is maintained at vacuum. The refrigerant containing space and the isolation valves 154 and 156 are not considered to be part of the inventive external fluid circuit 124 and are shown in FIG. 6 to fully disclose the intended use of the circuit 124.

To conduct the zero emissions testing of a refrigerant in a closed system, the testing tube container 110 is first supplied with a fresh testing tube 32 with the upstream end 40 and downstream end 42 thereof broken open. The external fluid circuit 124 of the present invention is then connected to the first isolation valve 154 and the second isolation valve 156 of the closed system as shown in FIG. 6. The needle valve 136 is closed and the three-way toggle valve 132 is adjusted to direct fluid flow out the first outlet port 132b and through the bypass loop 150. The compressor, if required, is turned on and the isolation valves 154 and 156 are opened allowing refrigerant to enter the external fluid circuit 124 up to the upstream port 136a of the needle valve 136. The needle valve 136 is then slowly opened to allow refrigerant to pass from the downstream port 136b into the upstream intake port 134a of the flow meter 134. At this point, refrigerant will be flowing through the bypass loop 150, but not the detecting loop 152, and back into the closed system through the small compressor 138 and second isolation valve 156.

The needle valve 136 is opened until a desired rate of flow, as indicated by flow line indicia 144, has been achieved. The three-way toggle valve 132 is then flipped to direct refrigerant out the second outlet port 132c into the detecting loop 152 and through the testing tube container 110 and testing tube 32. The test is timed as described above. During the test, the testing tube 32 will remove any acid and water in the refrigerant. The amount of water and acid present in the refrigerant can then be determined by the methods discussed above. After the test, the isolation valves 154 and 156 are closed and the external fluid circuit 124 is removed from the closed system.

There is thus shown an apparatus and method for testing for contaminants in a refrigerant in a variety of closed systems including systems having very low internal pressures without discharging the tested refrigerant into the atmosphere.

While this invention has been described in detail with reference to a preferred embodiment, it should be appreciated that the present invention is not limited to that precise embodiment. Rather, in view of the present disclosure, many modifications and variations would present themselves to those of skill in the art without departing from the scope and spirit of this invention, as defined in the appended claims.

What is claimed is:

1. Apparatus for testing for contaminates in a refrigerant in a closed system having a first and a second isolation valve, the apparatus comprising:

an external fluid circuit capable of being connected between the isolation valves allowing an amount of the refrigerant from the closed system to flow therethrough in a predetermined direction from the first to the second isolation valve when the isolation valves are open; the external circuit including detecting means for identifying contaminants within the refrigerant as the refrigerant flows therethrough, said detecting means being in series between said isolation valves and having an upstream end and a downstream end relative to the direction of refrigerant flow, flow meter means in series with said detecting means for determining the rate of flow of said refrigerant flowing through said external fluid circuit, said flow meter means being connected upstream of said detecting means;

flow regulator means for adjusting the flow of refrigerant through said external fluid circuit to a desired rate, said flow regulator means being upstream of said flow meter means; and three-way valve means for directing the flow of refrigerant through the circuit, said three-way valve means having an inlet port, a first outlet port, and a second outlet port, said inlet port being connected to receive the refrigerant from said flow meter means, and said second outlet port being connected to the upstream end of said detecting means; and a bypass line coupled to the first outlet port of the three way valve means and to a point downstream of the detecting means;

whereby when the isolation valves are open, the flow of refrigerant through said external fluid circuit can be first directed through said bypass line to bypass said detecting means when said three-way valve means has its first outlet port open and its second outlet port closed, thus allowing the flow through the circuit to be adjusted to the desired rate of flow by said flow regulator means, and can then be directed to flow through said detecting means by actuating said valve means so that its first outlet port is closed and its second outlet port is open, thus allowing said detecting means to identify contaminants in the refrigerant prior to the refrigerant being returned to the closed system.

2. The apparatus according to claim 1 further including compressor means having a suction line and a discharge line, the suction line being coupled to the bypass line and to the downstream end of said detecting means, the discharge line of said compressor means being coupled to the second isolation valve.

3. The apparatus according to claim 2 wherein said compressor means includes a hand-held compressor.

4. The method according to claim 3 including the further step of providing the external fluid circuit with three-way valve means for selectively directing the refrigerant flow through the bypass loop and the detecting loop.

5. The apparatus according to claim 1 wherein said flow meter means includes a transparent flow indicating chamber held vertically during operation and having a free-floating flow-responsive member contained therein and a flow line thereon to indicate the desired rate of flow.

6. The apparatus according to claim 5 wherein said flow regulator means includes a needle valve capable of adjusting the flow of refrigerant into said flow indicating chamber at an increasing rate to cause the free-floating member to reach the flow line thereby indicating that the desired rate of flow has been attained.

7. The apparatus according to claim 1 wherein said detecting means includes a testing tube and a testing tube holder, said testing tube holder including:

a generally elongate transparent container having oppositely disposed open ends, one of said open ends being an open upstream end and the other one of said open ends being an open downstream end, said container being adapted to removably contain therein said testing tube, a first coupling member connected to said open upstream end and having therein a passage in fluid communication with said container;

a first sealing means being adapted for providing a fluid tight fit between said first coupling member and said testing tube;

a second coupling member connected to said open downstream end and having therein a passage in fluid communication with said container; and a second sealing means being adapted for providing a fluid tight fit between said second coupling member and said container;

said testing tube including:

a single elongate tube member made of a generally transparent material and having oppositely disposed breakable ends, said ends of said tube member can be broken open to define respectively an upstream opening and a downstream opening;

an oil removal section adjacent said upstream end of said tube;

a first contaminant-indicating substance disposed in said tube member downstream of said oil removal section and adapted to remove and indicate the presence of water in the refrigerant flowing therethrough;

a second contaminant-indicating substance disposed downstream of said first contaminant indicating substance and being adapted to indicate the presence of acid in the refrigerant flowing therethrough; and means disposed between said first and second contaminant-indicating substances for preventing migrational action therebetween.

8. The apparatus according to claim 7 wherein said means disposed between said first and second contaminant-indicating substances includes a pair of fluid permeable partitions separated by screen means.

9. The apparatus according to claim 7 wherein said first contaminant-indicating substance includes cobaltous chloride on a silica sand base.

10. The apparatus according to claim 7 wherein said second contaminant-indicating substance includes bromophenol blue on a glycerol film coating a silica sand base.

11. A method for detecting the presence and amount of contaminants in a refrigerant, subject to contain oil, moisture and acid, flowing in a closed system having a first and a second isolation valve without causing discharge of the refrigerant from the closed system into the atmosphere, the method comprising the steps of:

removable connecting between said isolation valves an external fluid circuit having in parallel a bypass loop and a detecting loop allowing a limited amount of refrigerant from the closed system to flow through the circuit in a predetermined direction from the first isolation valve to the second isolation valve;

providing the external fluid circuit with a hand-held compressor pump to induce refrigerant flow through the circuit;

providing in series in the detecting loop of the external fluid circuit a testing tube capable of allowing the refrigerant flow to pass therethrough to detect contaminants in the refrigerant;

opening the isolation valves to allow the refrigerant to flow into the external fluid circuit through the bypass loop and back into the closed system through the second isolation valve;

regulating the flow of refrigerant through the external fluid circuit to a desired rate of flow;

directing the regulated flow at said desired rate to the detecting loop;

removing any oil present in the directed flow of refrigerant passing through the testing tube;

determining the amount of water present in the directed flow of refrigerant passing through the testing tube;

determining the amount of acid present in the directed flow of refrigerant passing through the testing tube; and returning said directed flow to the closed system through the second isolation valve.

12. The method according to claim 11 wherein said compressor is disposed downstream of said detecting loop.

13. A light-weight portable apparatus for testing for contaminates in a refrigerant in a closed system having a first and a second isolation valve, said apparatus comprising:

an external fluid circuit capable of being connected between the isolation valves to allow an amount of the refrigerant from the closed system to flow therethrough in a predetermined direction from the first to the second isolation valve when the isolation valves are open, said external circuit including;

detecting means for identifying contaminants within the refrigerant as tile refrigerant flows therethrough, said detecting means being engaged with the fluid circuit and having an upstream end and a downstream end relative to the direction of refrigerant flow;

flow regulator means for controlling the flow of refrigerant through said external fluid circuit to a desired rate; and flow meter means fluidly engaged with said detecting means for determining the rate of flow of said refrigerant flowing through said external fluid circuit.

14. The apparatus according to claim 13 wherein said flow meter means is connected upstream of said detecting means.

15. The apparatus according to claim 13 wherein said flow regulator means is positioned upstream of said flow meter means.

16. The apparatus according to claim 13 further including three-way valve means for directing the flow of refrigerant through the circuit, said three-way valve means having an inlet port, a first outlet port, and a second outlet port, said inlet port being connected to receive the refrigerant from said flow meter means, and said second outlet port being connected to the upstream end of said detecting means; and a bypass line coupled at one end to the first outlet port of the three-way valve means and at the other end back into the circuit at a predetermined point downstream of the detecting means so that when the isolation valves are open, the flow of refrigerant through said external fluid circuit can be directed through said bypass line to circumvent said detecting means when said three-way valve means has its first outlet port open and its second outlet port closed.

17. The apparatus according to claim 16 wherein the flow of refrigerant is directed to flow through said detecting means by actuating said valve means so that its first outlet port is closed and its second outlet port is open thereby allowing said detecting means to identify contaminants in the refrigerant prior to the refrigerant being returned to the closed system.

18. The apparatus according to claim 16 further including compressor means having a suction line and a discharge line wherein said suction line is coupled into said bypass line and the downstream end of said detecting means, and said discharge line of said compressor means is coupled into the second isolation valve.

19. The apparatus according to claim 18 wherein said compressor means includes a hand-held compressor.

20. The apparatus according to claim 13 wherein said flow meter means includes a transparent flow indicating chamber positioned vertically during operation, the chamber having a free-floating flow-responsive member contained therein and a flow line thereon to indicate the desired rate of flow.

21. The apparatus according to claim 20 wherein said flow regulator means is adjustable and includes a needle valve capable of adjusting the flow of refrigerant into said flow indicating chamber at an increasing rate to cause the free-floating member to reach the flow line thereby indicating that the desired rate of flow has been attained.

22. The apparatus according to claim 13 wherein said detecting means includes a testing tube and a testing tube holder, said testing tube holder including:

a generally elongate transparent container having oppositely disposed open ends, one of said open ends being an open upstream end and the other one of said open ends being an open downstream end, said container being adapted to removably contain therein said testing tube;

a first coupling member connected to said open upstream end and having therein a passage in fluid communication with said container;

a first sealing means being adapted for providing a fluid-tight fit between said first coupling member and said testing tube;

a second coupling member connected to said open downstream end and having therein a passage in fluid communication with said container; and a second sealing means being adapted for providing a fluid-tight fit between said second coupling member and said container.

23. The apparatus according to claim 22 wherein said testing tube includes:

a single elongate tube member made of a generally transparent material and having oppositely disposed breakable ends, said ends of said tube member capable of breaking open to define, respectively, an upstream opening and a downstream opening;

an oil removal section adjacent said upstream end of the tube member;

a first contaminant-indicating substance being disposed in the tube member downstream of said oil removal section and adapted to indicate and remove the presence of water in the refrigerant flowing therethrough;

a second contaminant-indicating substance being disposed downstream of said first contaminant-indicating substance and adapted to indicate the presence of acid in the refrigerant flowing therethrough; and means disposed between said first and second contaminant-indicating substances for preventing migrational action therebetween.

24. The apparatus according to claim 23 wherein said means disposed between said first and second contaminant-indicating substances includes a pair of fluid permeable partitions separated by screen means.

25. The apparatus according to claim 23 wherein said first contaminant-indicating substance includes cobaltous chloride on a silica sand base.

26. The apparatus according to claim 23 wherein said second contaminant-indicating substance includes bromophenol blue on a glycerol film coating a silica sand base.

* * * * *